(12) United States Patent
Kane et al.

(10) Patent No.: US 9,095,700 B2
(45) Date of Patent: Aug. 4, 2015

(54) LEAD POSITIONING AND FIXATION SYSTEM

(75) Inventors: Lawrence Kane, Roseville, MN (US); Elliot W. Bridgeman, Big Lake, MN (US); John Swoyer, Blaine, MN (US)

(73) Assignee: Greatbach Ltd., Clarence, NY (US)

( * ) Notice: Subject to any disclaimer, the term of this patent is extended or adjusted under 35 U.S.C. 154(b) by 106 days.

(21) Appl. No.: 13/571,987

(22) Filed: Aug. 10, 2012

(65) Prior Publication Data
US 2014/0046413 A1 Feb. 13, 2014

(51) Int. Cl.
| A61N 1/00 | (2006.01) |
| A61N 1/05 | (2006.01) |
| A61F 2/90 | (2013.01) |
| A61B 18/00 | (2006.01) |
| A61B 18/14 | (2006.01) |

(52) U.S. Cl.
CPC ........... *A61N 1/0558* (2013.01); *A61B 18/1492* (2013.01); *A61B 2018/00214* (2013.01); *A61B 2018/00285* (2013.01); *A61F 2/90* (2013.01); *A61N 1/057* (2013.01); *A61N 2001/058* (2013.01)

(58) Field of Classification Search
CPC ................. A61B 18/1492; A61B 2018/00214; A61B 2018/00285; A61B 1/057; A61B 2001/058; A61B 2/90
USPC .................................. 607/115, 116, 126–128
See application file for complete search history.

(56) References Cited

U.S. PATENT DOCUMENTS

| 6,510,347 B2 | 1/2003 | Borkan |
| 7,149,587 B2 * | 12/2006 | Wardle et al. ................. 607/126 |
| 7,684,873 B2 | 3/2010 | Gerber |
| 7,904,149 B2 | 3/2011 | Gerber |
| 8,043,126 B2 | 10/2011 | Bjorklund et al. |
| 8,260,436 B2 | 9/2012 | Gerber et al. |
| 2002/0177888 A1 | 11/2002 | Williams et al. |
| 2007/0179583 A1 * | 8/2007 | Goetzinger et al. .......... 607/126 |
| 2008/0103572 A1 | 5/2008 | Gerber |
| 2008/0103574 A1 | 5/2008 | Gerber |
| 2008/0183263 A1 | 7/2008 | Alexander |
| 2009/0210043 A1 | 8/2009 | Reddy |
| 2010/0137928 A1 | 6/2010 | Duncan et al. |
| 2011/0054581 A1 | 3/2011 | Desai et al. |
| 2011/0054584 A1 | 3/2011 | Alexander et al. |
| 2011/0160830 A1 | 6/2011 | Morris et al. |
| 2011/0218603 A1 | 9/2011 | Victorine et al. |
| 2012/0035616 A1 | 2/2012 | Olsen et al. |

* cited by examiner

*Primary Examiner* — Niketa Patel
*Assistant Examiner* — Lindsey G Hankins
(74) *Attorney, Agent, or Firm* — Michael P. Horvath

(57) ABSTRACT

A therapy assembly configured for at least partial insertion in a living body. A plurality of fixation structures are disposed radially around the therapy delivery element proximate the electrodes. The fixation structures include wires having a diameter in a range between about 0.004 inches and about 0.020 inches. The wires have a first end attached to the therapy delivery element and a second end attached to a sliding member configured to slide along the therapy delivery element. The fixation structures are configured to collapse inward to a collapsed configuration when inserted into a lumen of an introducer and to deploy to a deployed configuration when the introducer is retracted. A fitting is located at proximal end of the introducer that releasably locks the therapy delivery element to the introducer, such that torque applied to the fitting is substantially transmitted to the distal end of the therapy assembly.

23 Claims, 14 Drawing Sheets

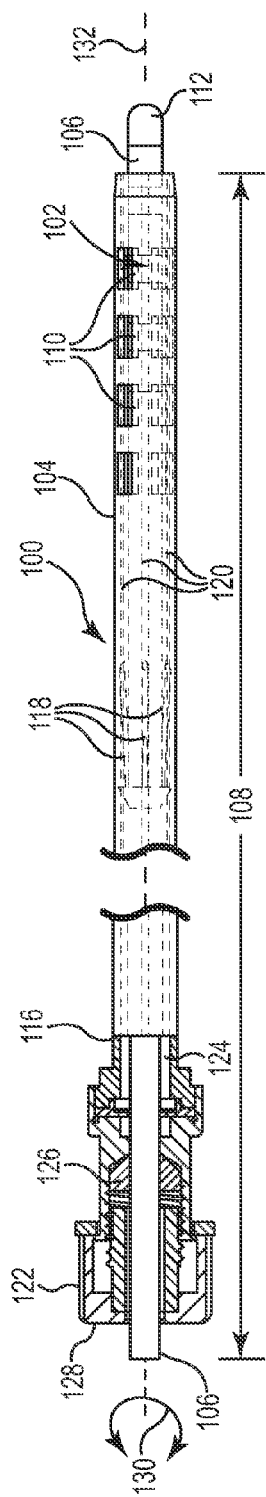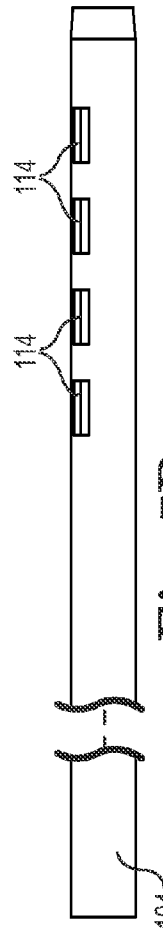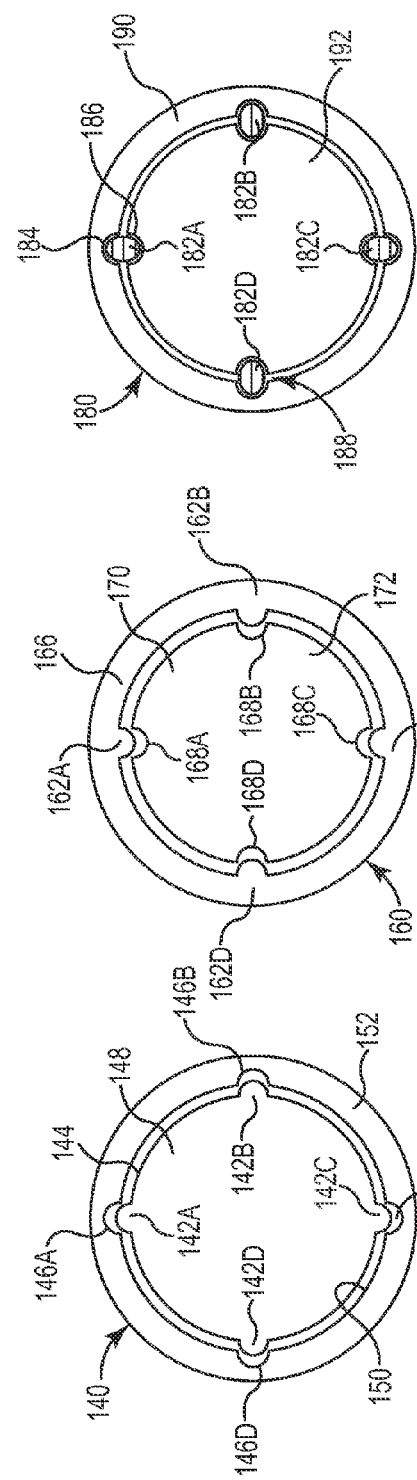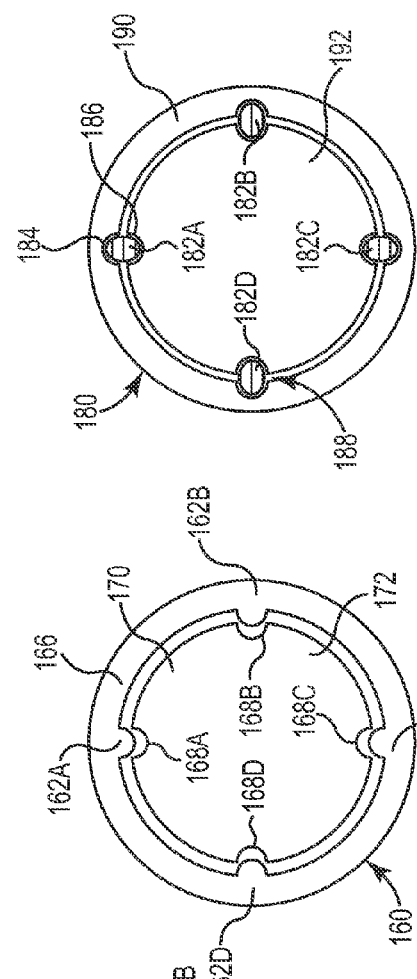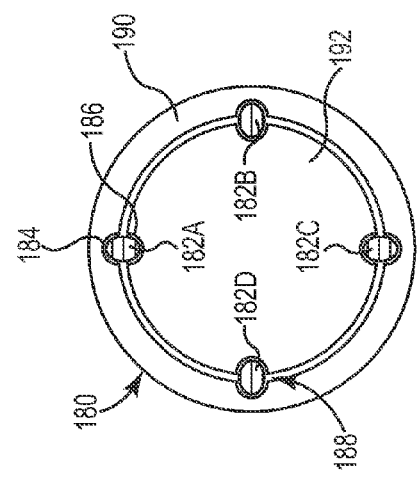

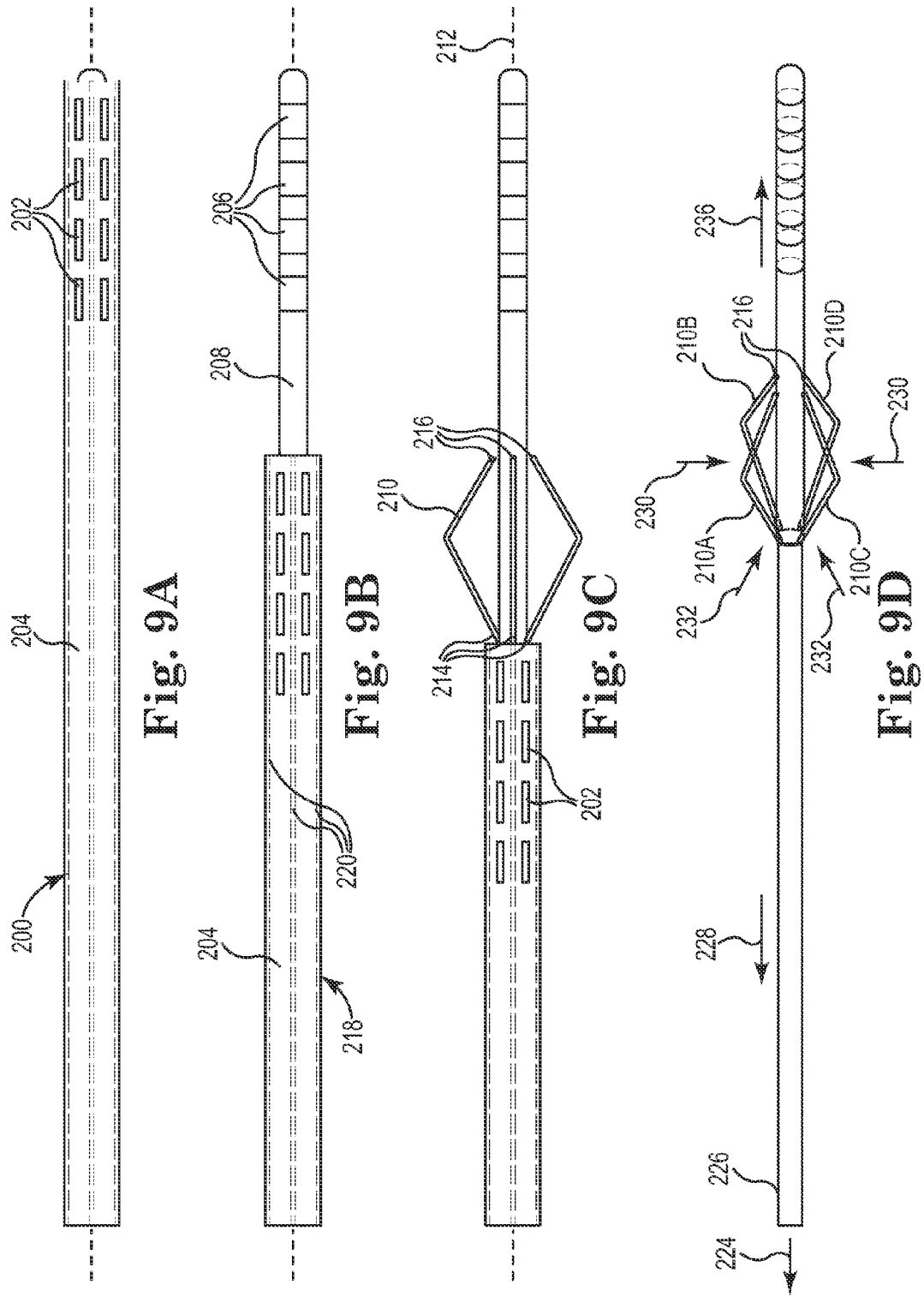

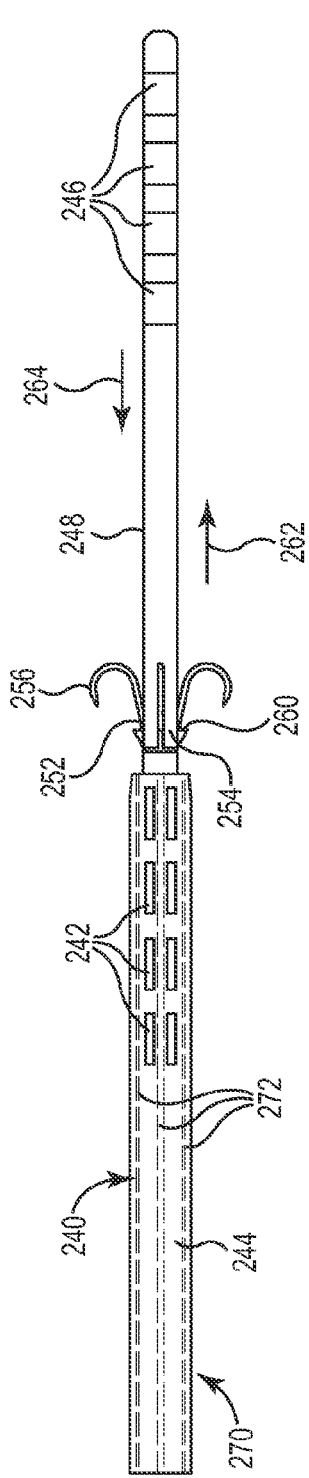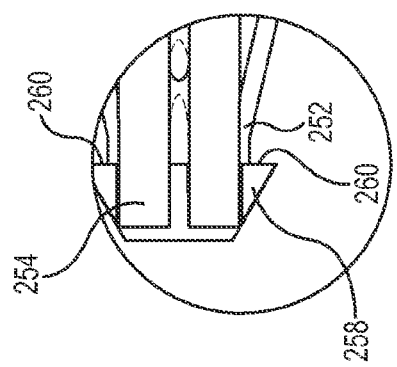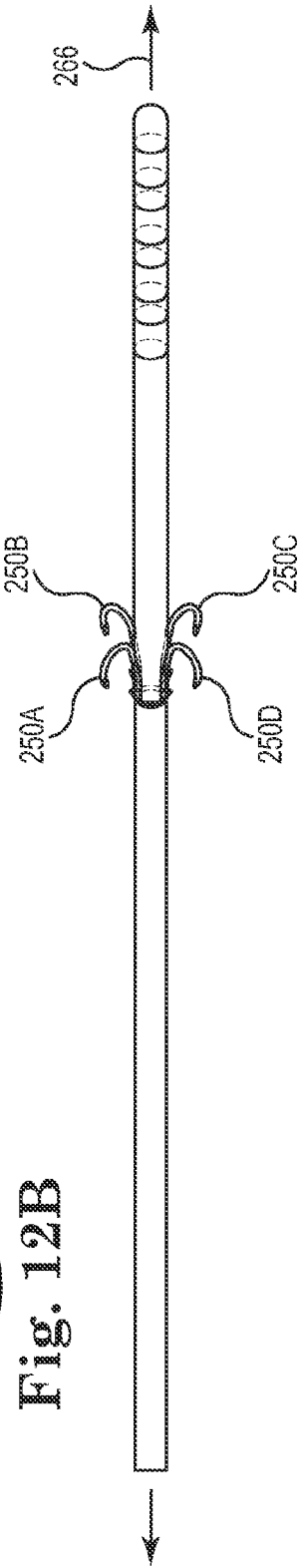
Fig. 12A
Fig. 12B
Fig. 12C

LEAD POSITIONING AND FIXATION SYSTEM

FIELD

The present disclosure is directed to a method and apparatus that allows for stimulation of body tissue, particularly nerves. More specifically, the implantable medical electrical lead is held in a fixed rotational orientation relative to an introducer to permit precise rotational orientation of the electrodes during implantation. The implantable medical electrical lead includes fixation structures that provide stability of the stimulation electrode and lead. Moreover, this disclosure relates to the method of implantation and anchoring of the medical electrical lead electrodes in operative relation to a selected nerve to allow for stimulation.

BACKGROUND

Implantable medical electronics devices consist of an implanted pulse generator that is used to provide electrical stimulation to certain tissues and an implantable lead or leads that are used to transmit the electrical impulse to the targeted tissues. Examples include cardiac pacemaking, and a number of related applications for cardiac rhythm management, treatments for congestive heart failure, and implanted defibrillators. Other applications for implantable pulse generators include neurostimulation with a wide range of uses such as pain control, nervous tremor mitigation, incontinent treatment, epilepsy seizure reduction, vagus nerve stimulation for clinical depression, and the like.

Despite various suture fixation devices, nerve stimulation leads can be dislodged from the most efficacious location due to stresses placed on the lead by the ambulatory patient. A surgical intervention is then necessary to reposition the electrode and affix the lead. The implantable pulse generator ("IPG") is programmed to deliver stimulation pulse energy to the electrode providing the optimal nerve response. The efficacy of the selected electrode can fade over time due to dislodgement or other causes.

Physicians spend a great deal of time with the patient under a general anesthetic placing the small size stimulation electrodes relative to the target nerves. The patient is thereby exposed to the additional dangers associated with extended periods of time under a general anesthetic. Movement of the lead, whether over time from suture release or during implantation during suture sleeve installation, is to be avoided. As can be appreciated, unintended movement of any object positioned proximate a nerve may cause unintended nerve damage. Moreover reliable stimulation of a nerve requires consistent nerve response to the electrical stimulation that, in turn, requires consistent presence of the stimulation electrode proximate the target nerve. On the other hand, if the target nerve is too close to the electrode, inflammation or injury to the nerve can result, diminishing efficacy and possibly causing patient discomfort.

Cardiac pacing leads are commonly provided with passive fixation mechanisms that non-invasively engage heart tissue in a heart chamber or cardiac blood vessel or active fixation mechanisms that invasively extend into the myocardium from the endocardium or epicardium. Endocardial pacing leads having pliant tines that provide passive fixation within interstices of trabeculae in the right ventricle and atrial appendage are well known in the art as exemplified by U.S. Pat. Nos. 3,902,501, 3,939,843, 4,033,357, 4,236,529, 4,269,198, 4,301,815, 4,402,328, 4,409,994, and 4,883,070, for example. Such tined leads typically employ tines that extend outwardly and proximally from a band proximal to a distal tip pace/sense electrode and that catch in natural trabecular interstices when the distal tip electrode is advanced into a trial appendage or the ventricular apex.

Certain spinal cord stimulation leads have been proposed employing tines and/or vanes as stand-offs to urge the stimulation electrode in the epidural space toward the spinal cord as disclosed in U.S. Pat. Nos. 4,590,949 and 4,658,535, for example, and to stabilize the stimulation electrode in the epidural space as disclosed in U.S. Pat. No. 4,414,986, for example.

Stimulation leads for certain pelvic floor disorders have been proposed with a fixation mechanism that includes a plurality of tine elements arrayed in a tine element array along a segment of the lead proximal to the stimulation electrode array, such as for example in U.S. Pat. Nos. 6,999,819; 7,330,764; 7,912,555; 8,000,805; and 8,036,756. Each tine element includes a plurality of flexible, pliant, tines. The tines are configured to be folded inward against the lead body when fitted into and constrained by the lumen of an introducer.

Peripheral nerve field stimulation ("PNFS") involves delivery of stimulation to a specific peripheral nerve via one or more electrodes implanted proximate to or in contact with a peripheral nerve, such as disclosed in U.S. Pat. Publication No. 2009/0281594. PNFS may be used to deliver stimulation to, for example, the vagal nerves, cranial nerves, trigeminal nerves, ulnar nerves, median nerves, radial nerves, tibial nerves, and the common peroneal nerves. When PNFS is delivered to treat pain, one or more electrodes are implanted proximate to or in contact with a specific peripheral nerve that is responsible for the pain sensation.

During the implantation procedure the surgeon selectively activates the electrodes to test nerve response (also referred to as "mapping") to determine optimal lead position. If the lead is contained in an introducer during the mapping operation, openings are provided in the introducer to permit the stimulation electrodes to engage with the targeted nerve tissue. As a result, the axial position of the introducer relative to the electrodes is critical so the openings in the introducer are positioned opposite the targeted nerve tissue.

Due to the length and flexibility of typical introducers and leads, torque applied by the surgeon at the proximal end during implantation can cause the lead to be displaced relative to the openings in the sheath. Also, the torque is not always transmitted uniformly to the distal end of the introducer and/or lead, complicating lead placement. In particular, only a portion of the torque applied at the proximal end is typically transmitted to the distal end.

Torque applied to the introducer and/or lead during implantation may also be stored in the system. The release of this stored energy, such as during withdrawal of the introducer, can displace the electrodes relative to the target nerve tissue.

Fixation structures on the lead are typically restrained by the introducer during lead placement. Optimal lead placement must be achieved before deploying any fixation structures. If the fixation structures on the lead are permitted to deploy into the openings in the introducer, the two components can become interlocked, preventing removal of the introducer without substantial disruption to the lead.

BRIEF SUMMARY

The present disclosure is directed to a therapy assembly configured for at least partial insertion in a living body. The therapy assembly includes a therapy delivery element with a proximal end having a plurality of electrical contacts configured to electrically couple with an implantable pulse generator and a distal end with a plurality of electrodes that are electrically coupled to the electrical contacts at the proximal end. An introducer with a lumen is configured to receive the therapy delivery element. A plurality of fixation structures are disposed radially around the therapy delivery element proximate the electrodes. The fixation structures include wires having a diameter in a range between about 0.004 inches and about 0.020 inches. The wires have a first end attached to the therapy delivery element and a second end attached to a sliding member configured to slide along the therapy delivery element. The fixation structures are configured to collapse inward to a collapsed configuration when inserted into the lumen of the introducer and to deploy to a deployed configuration when the introducer is retracted. A fitting is located at proximal end of the introducer that releasably locks the therapy delivery element to the introducer, such that torque applied to the fitting is substantially transmitted to the distal end of the therapy assembly.

The fixation structures are configured to provide generally symmetrical resistance to displacement of the therapy delivery element within the living body in either a proximal direction or a distal direction along a central axis. The fixation structures are located generally symmetrical relative to a central axis of the therapy delivery element.

In one embodiment, the introducer includes a plurality of openings generally aligned with the electrodes. The fixation structures are preferably radially offset from the openings in the introducer. A plurality of axially oriented grooves is preferably located on the inner surface of the introducer. The plurality of fixation structures is retained in sliding engagement with the axial grooves in the collapsed configuration. The sliding engagement of the fixation structures in the axially oriented grooves maintains rotational alignment of openings in the introducer with the electrodes and prevents the fixation structures from deploying in the openings.

Between about 90 percent to about 100 percent of torque applied to the fitting is preferably transmitted to the distal end of the therapy assembly.

In another embodiment, the therapy assembly includes at least one pair of opposing axially oriented grooves located on the outer surface of the therapy delivery element and the inner surface of the introducer. A discrete structure is slid into engagement with both of the opposing axially oriented grooves. In another embodiment, the fixation structures are attached to a fastener that is bonded to the therapy delivery element. The fastener preferably includes at least one surface oriented to resist displacement of the therapy delivery element in a distal direction.

The present disclosure is also directed to a neurostimulation system including an implantable pulse generator and a therapy assembly as disclosed herein.

The present disclosure is also directed to a method of implanting a therapy assembly in a living body. The method includes the steps of inserting an introducer adjacent into the living body with a distal end adjacent an implantation site. A distal end of the therapy delivery element is slid into the introducer to compress wire fixation structures with a diameter in a range of between about 0.004 inches to about 0.020 inches to a collapsed configuration within the lumen. A sliding member attached to one end of the wire fixation structures is displaced along the therapy delivery element as the wire fixation structure are compressed to the collapsed configuration. The therapy delivery element is advanced into the introducer until electrodes near the distal end of the therapy delivery element extend beyond a distal end of the introducer. Placement of the therapy delivery element in the living body is confirmed by activating the electrodes to stimulate the living body. The therapy delivery element is secured to a fitting attached to a proximal end of the introducer. Torque is applied to the fitting such that between about 90 percent to about 100 percent of the torque is transmitted to the distal end of the therapy assembly. The therapy delivery element is release from the fitting. The introducer is retracted to deploy the fixation structures to a deployed configuration.

BRIEF DESCRIPTION OF THE DRAWINGS

FIG. 7A illustrates a therapy assembly including interlock features connecting an introducer to a therapy delivery element located within the introducer in accordance with an embodiment of the present disclosure.

FIG. 7B illustrates the introducer of FIG. 7A.

FIGS. 8A-8C are cross-sectional views of various interlocking structures in accordance with certain embodiments of the present disclosure.

FIG. 9A illustrates a therapy assembly with electrodes exposed through openings in an introducer in accordance with an embodiment of the present disclosure.

FIG. 9B illustrates the introducer of FIG. 9A retracted to expose the electrodes in accordance with an embodiment of the present disclosure.

FIG. 9C illustrates the introducer of FIG. 9A retracted to deploy fixation structures in accordance with an embodiment of the present disclosure.

FIG. 9D illustrates the introducer of FIG. 9A removed in accordance with an embodiment of the present disclosure.

FIG. 12A illustrates an alternate therapy assembly with an introducer retracted to deploy fixation structures in accordance with an embodiment of the present disclosure.

FIG. 12B illustrates a fastener retaining fixation structures to the therapy delivery element of FIG. 12A.

FIG. 12C illustrates the introducer of FIG. 12A removed in accordance with an embodiment of the present disclosure.

The drawings are not necessarily to scale. Like numbers refer to like parts or steps throughout the drawings.

DETAILED DESCRIPTION OF SOME EMBODIMENTS

The description that follows highlights spinal cord stimulation (SCS) system, the treatment of pelvic floor disorders, and peripheral nerve field stimulation (PNFS). However, it is to be understood that the disclosure relates to any type of implantable therapy delivery system with one or more therapy delivery elements with one or more electrodes or sensors. For example, the present disclosure may be used as part of a pacemaker, a defibrillator, a cochlear stimulator, a retinal stimulator, a stimulator configured to produce coordinated limb movement, a cortical stimulator, a deep brain stimulator, microstimulator, or in any other neural stimulator configured to treat sleep apnea, shoulder sublaxation, headache, etc.

In another embodiment, one or more of the therapy delivery elements may be a fluid or drug delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be a medical electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof. "Target tissue site" refers generally to the target site for implantation of a therapy delivery element, regardless of the type of therapy.

Figure 1:
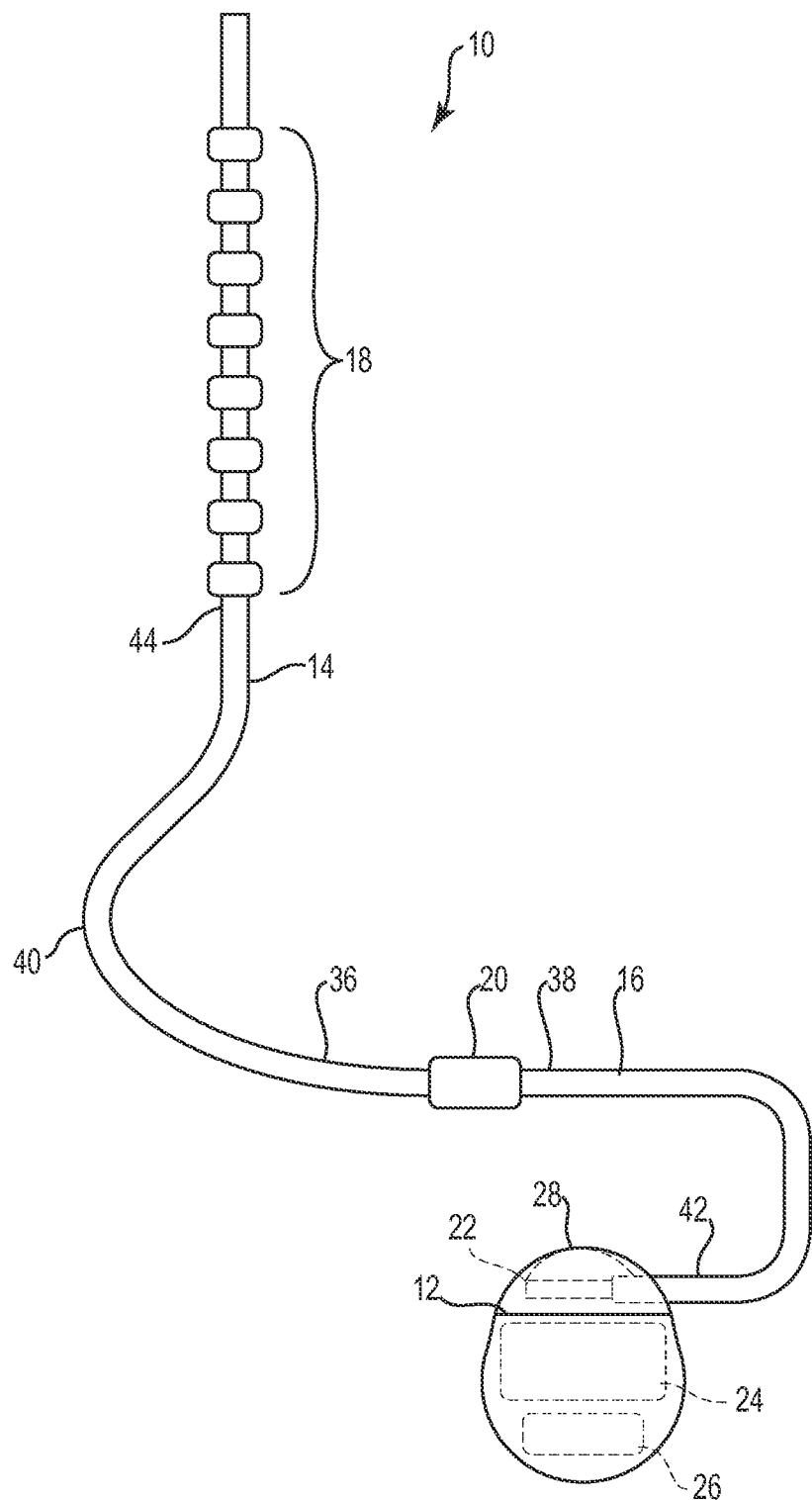
FIG. 1 is a schematic illustration of a therapy delivery system.

FIG. 1 illustrates a generalized therapy delivery system 10 that may be used in stimulation applications. The therapy delivery system 10 generally includes an implantable pulse generator 12 ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter ranging between about 0.03 inches to about 0.07 inches and a length ranging between about 30 cm to about 90 cm for spinal cord stimulation applications. The lead body 40 may include a suitable electrically insulative coating, such as, a polymeric material (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2A:
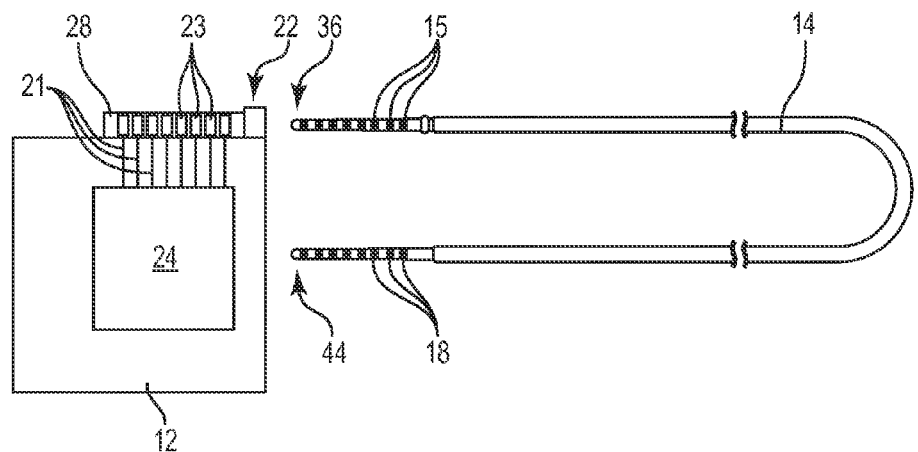
FIG. 2A is a schematic illustration of an implantable pulse generator and a therapy delivery element in accordance with an embodiment of the present disclosure.

FIG. 2A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22. In the embodiment illustrated in FIGS. 2A and 2B, the therapy delivery element 14 forms a medical electrical lead.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can be configured to independently deliver electrical impulses to each of the electrodes 18.

Figure 2B:
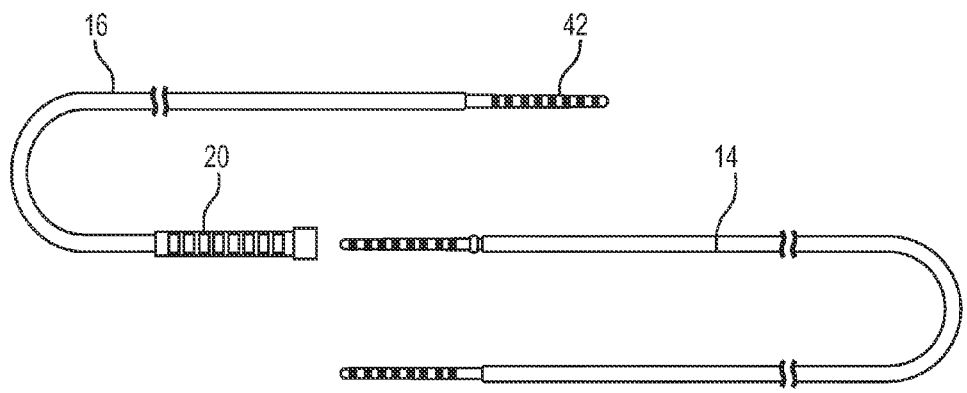
FIG. 2B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 2B. The connector 20 at the distal end 38 of the lead extension 16 preferably includes a plurality of the contacts 23 configured in a manner similar to the connector assembly 22.

Figure 3:
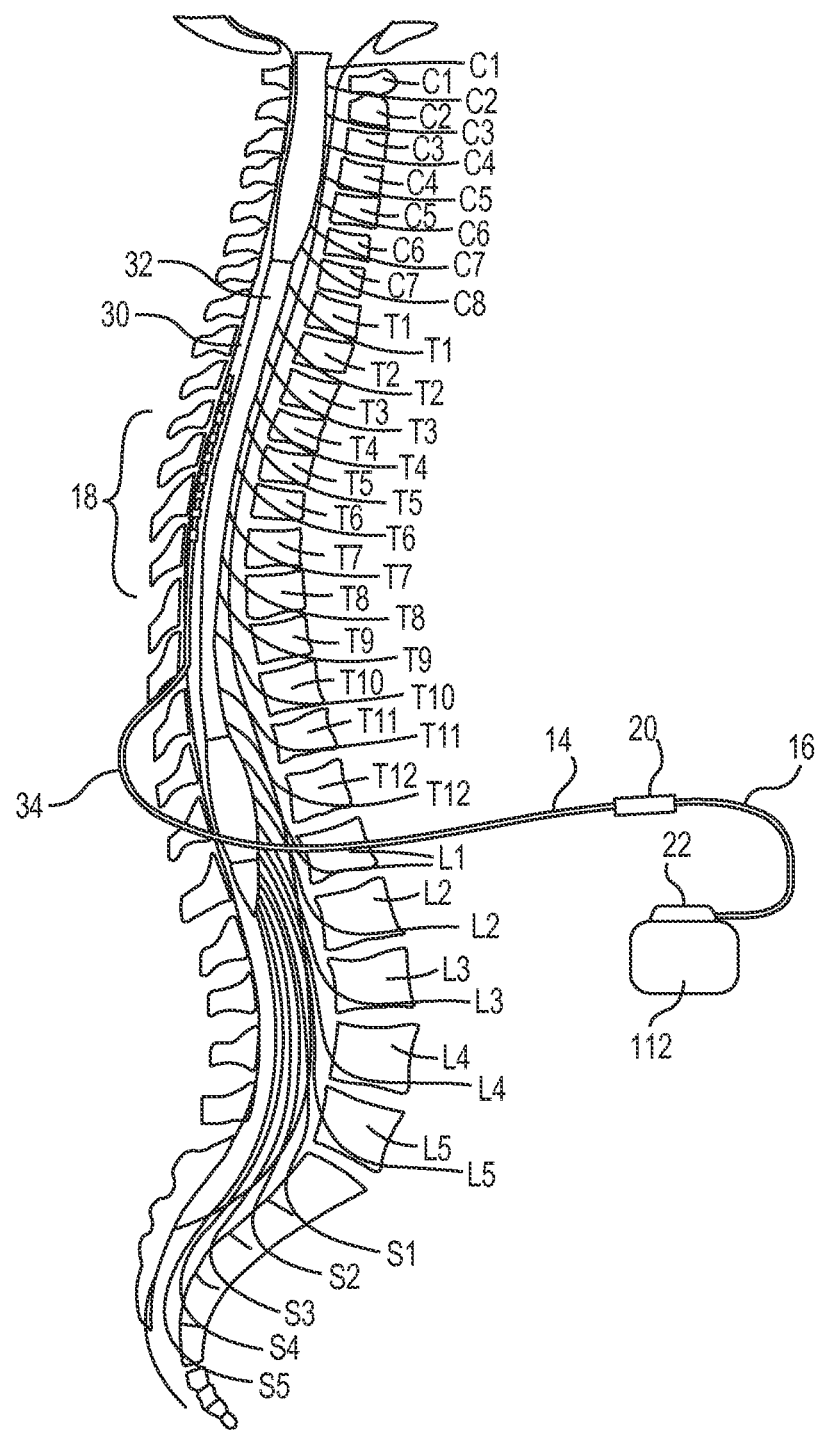
FIG. 3 is a schematic illustration of a therapy delivery system for spinal cord stimulation in accordance with an embodiment of the present disclosure.

FIG. 3 illustrates the therapy delivery element 14 used for spinal cord stimulation (SCS) implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 4:
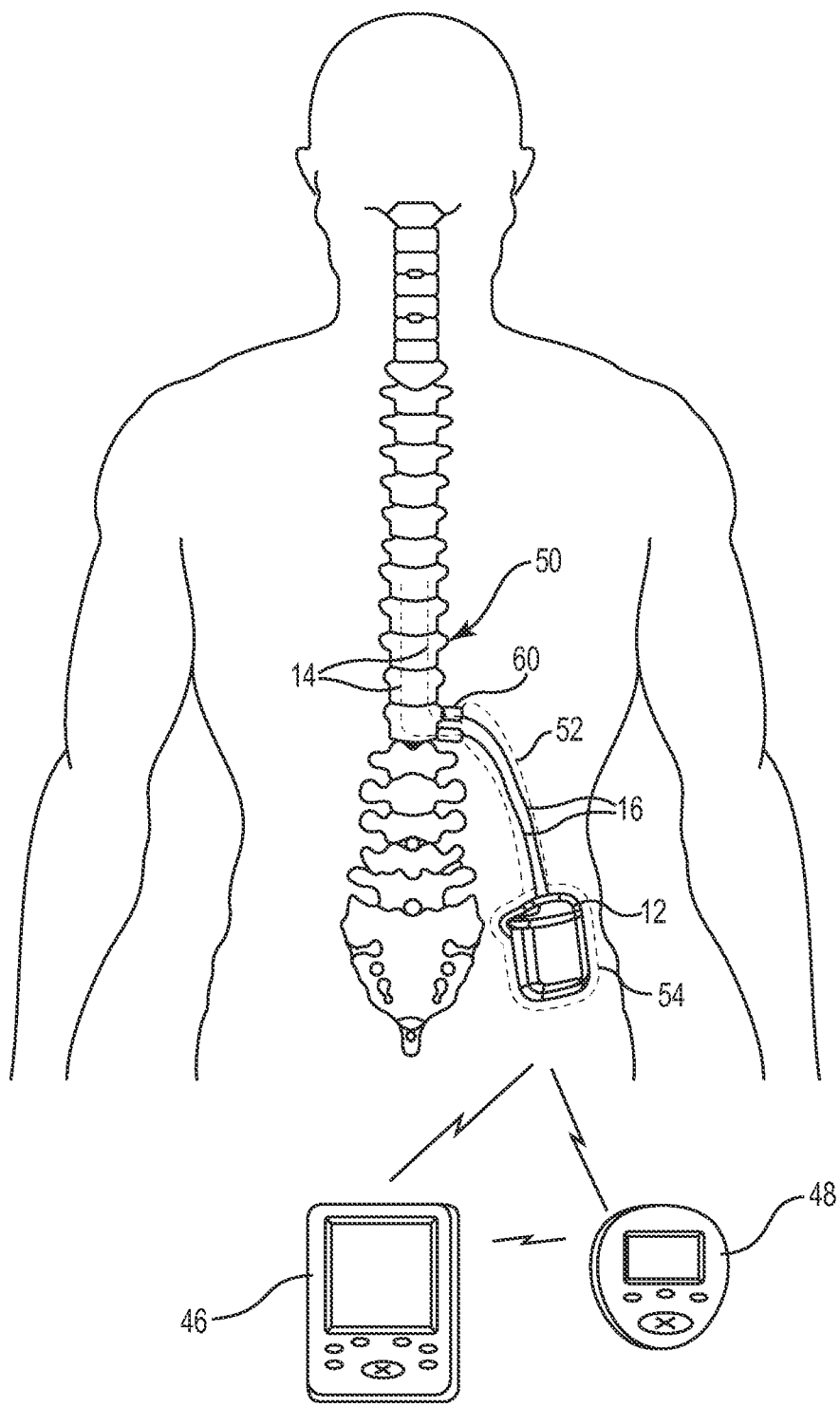
FIG. 4 is an alternate illustration of an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 4. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 4, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" may be used interchangeably, unless context indicates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 5:
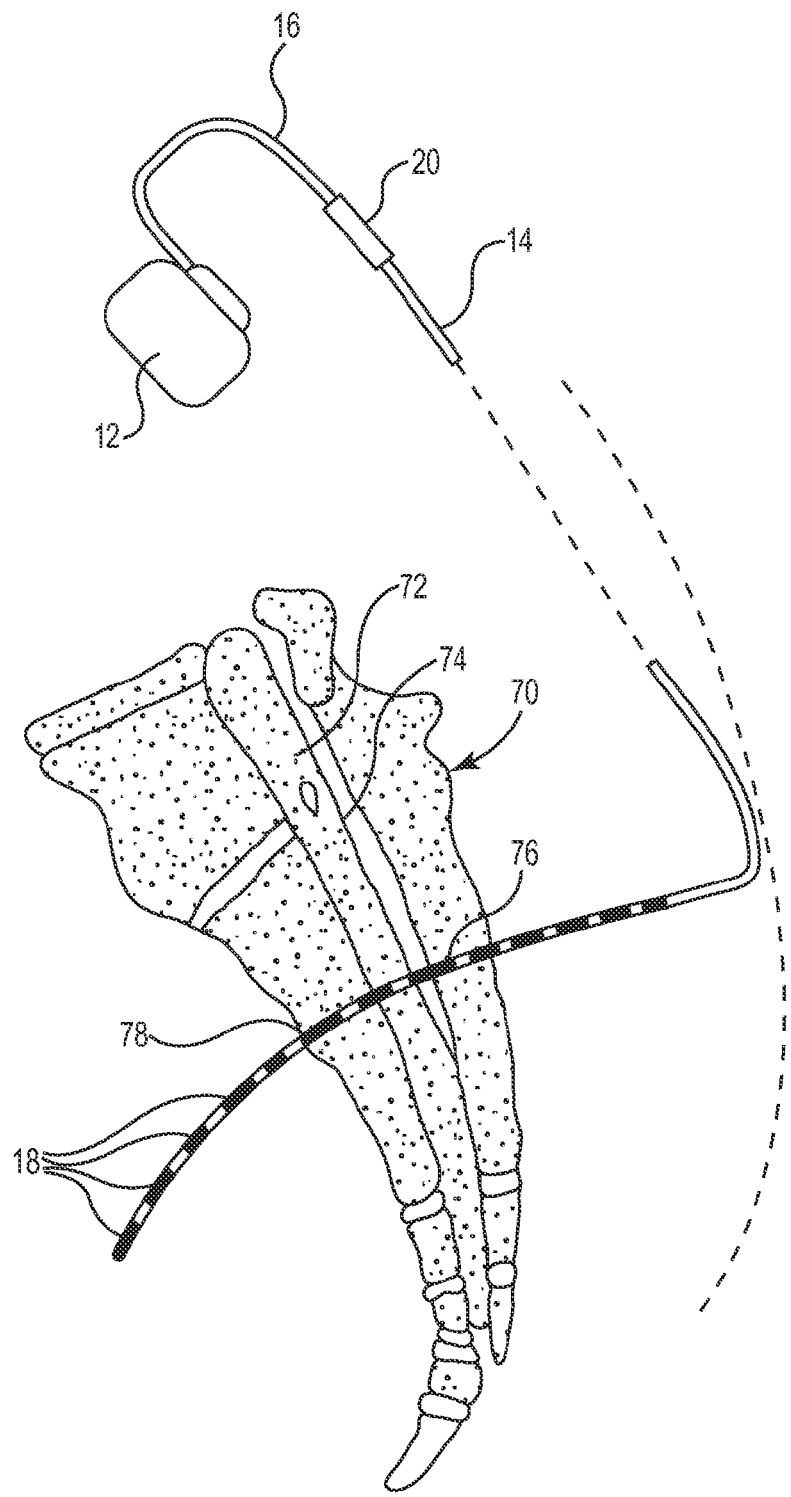
FIG. 5 is a schematic illustration of a therapy delivery system for treating pelvic floor disorders in accordance with an embodiment of the present disclosure.

FIG. 5 illustrates the therapy delivery element 14 used for pelvic floor disorders such as, urinary incontinence, urinary urge/frequency, urinary retention, pelvic pain, bowel dysfunction (constipation, diarrhea), erectile dysfunction, are bodily functions influenced by the sacral nerves. The organs involved in bladder, bowel, and sexual function receive much of their control via the second, third, and fourth sacral nerves, commonly referred to as S2, S3 and S4 respectively. Electrical stimulation of these various nerves has been found to offer some control over these functions. Several techniques of electrical stimulation may be used, including stimulation of nerve bundles 72 within the sacrum 70. The sacrum 70, generally speaking, is a large, triangular bone situated at the lower part of the vertebral column, and at the upper and back part of the pelvic cavity. The spinal canal 74 runs throughout the greater part of the sacrum 70. The sacrum is perforated by the posterior sacral foramina 76 and anterior sacral foramina 78 that the sacral nerves 70 pass through.

Specifically, urinary incontinence is the involuntary control over the bladder that is exhibited in various patients. The therapy delivery element 14 is percutaneously implanted through the foramina 76, 78 of the sacral segment S3 for purposes of selectively stimulating the S3 sacral nerve 72. Stimulation energy is applied through the lead 14 to the electrodes 18 to test the nerve response. The electrodes 18 are moved back and forth to locate the most efficacious location, and the lead 14 is then secured by suturing the lead body to subcutaneous tissue posterior to the sacrum 70 and attached to the output of a neurostimulator IPG 12.

Figure 6:
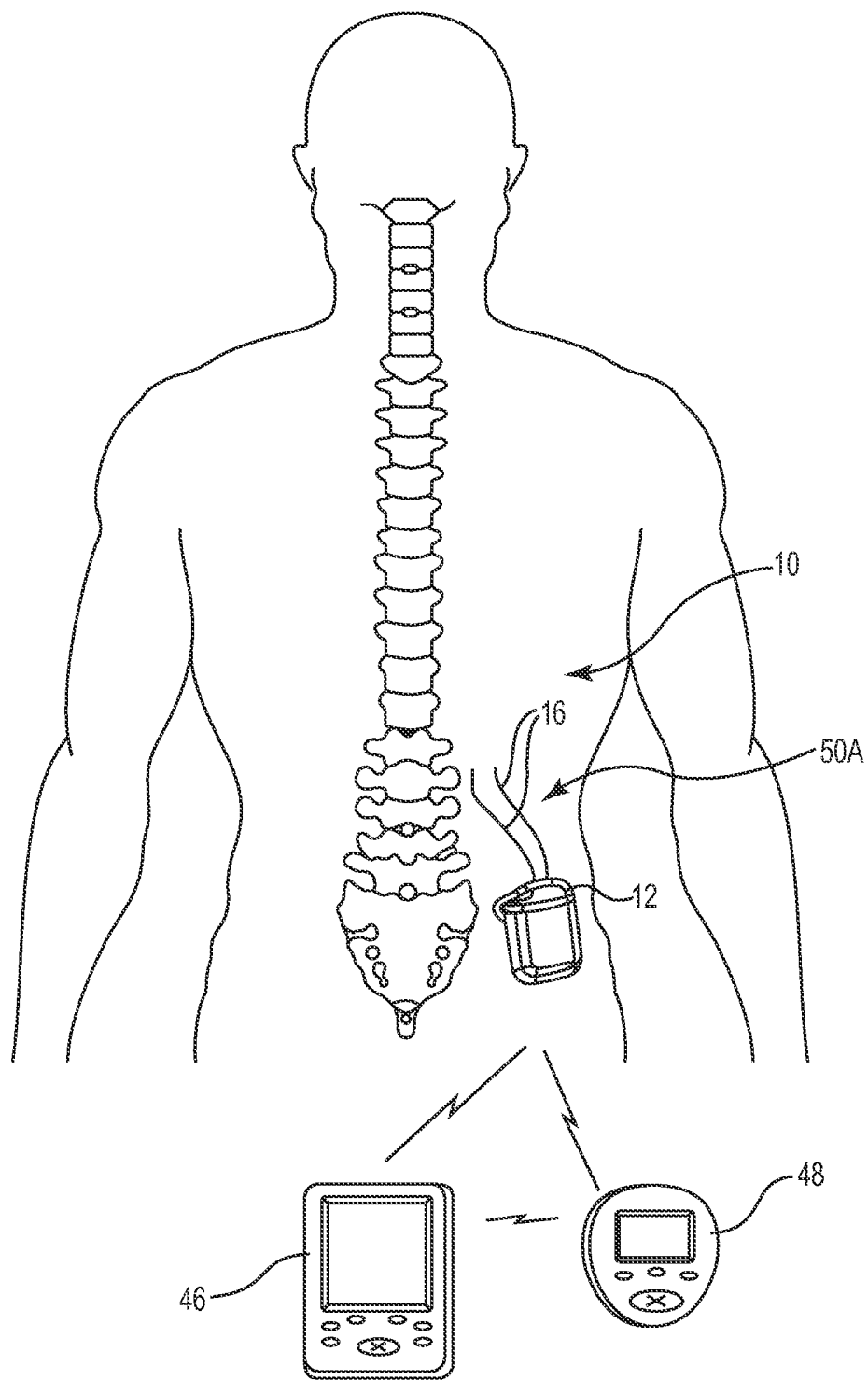
FIG. 6 is a schematic illustration of a therapy delivery system for peripheral nerve stimulation in accordance with an embodiment of the present disclosure.

FIG. 6 illustrates the therapy delivery element 14 used for delivering peripheral nerve field stimulation (PNFS) to a patient. Therapy delivery element 14 delivers PNFS from the implantable pulse generator 12 to the tissue of patient at target location 50A where patient experiences pain. Clinician programmer 46 and patient programmer 48 may communicate via wireless communication with the implantable pulse generator 12.

Therapy delivery element 14 may be implanted within or between, for example, intra-dermal, deep dermal, or subcutaneous tissue of patient at the location 50A where patient experiences pain. Subcutaneous tissue includes skin and associated nerves, and muscles and associated nerves or muscle fibers. In the illustrated example, location 50A is a region of the lower back. In other examples, the therapy delivery element 14 may extend from implantable pulse generator 12 to any localized area or dermatome in which patient experiences pain, such as various regions of the back, the back of the head, above the eyebrow, and either over the eye or under the eye, and may be used to treat failed back surgery syndrome (FBBS), cervical pain (e.g., shoulder and neck pain), facial pain, headaches supra-orbital pain, inguinal and pelvic pain, chest and intercostal pain, mixed pain (e.g., nociceptive and neuropathic), visceral pain, neuralgia, peroneal pain, phantom limb pain, and arthritis.

FIG. 7A illustrates a therapy assembly 100 including one or more interlock features 102 connecting an introducer 104 to a therapy delivery element 106 in accordance with an embodiment of the present disclosure. As will be discussed in connection with the various embodiments, the interlock features 102 can be located at discrete locations along the length 108 of the introducer 104, or can extend along the entire length 108 thereof.

The therapy delivery element 106 includes a plurality of ring electrodes 110 near distal end 112 (see also, FIG. 9B). The electrodes 110 are positioned opposite openings 114 in the introducer 104 (see FIG. 7B) to permit engagement with the target nerve tissue during testing and implantation. In use, the surgeon positions the therapy assembly 100 adjacent to the target nerve tissue using known techniques (see e.g., FIG. 11). The interlock features 102 align the electrodes 110 with openings 114 in the introducer 104 and increase the efficiency of torque transmission along the length 108 of the introducer 104. The openings 114 are positioned opposite the target nerve tissue. The energized electrodes 110 stimulate the adjacent nerve tissue through the openings 114.

The openings 114 can be a variety of shapes, such as rectangular, circular, oval, or any regular or irregular shape. The area of the openings 114 is preferably maximized in order to maximize exposed surface area of the electrodes 110. The electrodes 110 typically have an outside diameter of about 0.055 inches and a length of in a range between about 0.060 inches and about 0.120 inches. The openings 114 preferably have a surface area in a range between about 0.010 square inches to about 0.021 square inches. The openings 114 in the introducer 104 preferably expose at least 50%, and preferably at least 75% of available surface area of the electrodes 110.

The introducer 104 can be made from a variety of flexible bio-compatible polymeric or metal materials, such as for example, polyethylene terephthalate (PET), Nylon, polyproylene, high-performance polyethylenes, poly-L-lactide (PLLA), or polycaprolactone (PCL), urethane, silicone, Teflon, or any combination of these materials.

The embodiment of FIG. 7A includes interlock features 102 located near the electrodes 110 and fitting 122 located near proximal end 116 of the introducer 104. The interlock features 102 includes one or more fixation structures 118 configured to slide along central axis 132 in grooves 120 formed along inside surface of the introducer 104 when in a collapsed configuration (see e.g., FIGS. 9C and 10A). The fitting releasably couples to both the proximal end 116 of the introducer 104 and the therapy delivery element 106. In particular, proximal end 116 of the introducer 104 is bonded to sleeve 124. Therapy delivery element 106 is captured in the fitting 122 o-ring 126 compressed by rotating threaded cap 128. Consequently, torque 130 applied to the fitting 122 is transmitted by both the introducer 104 and the therapy delivery element 106 to the distal end 112.

The present fixation structures 102 torsionally couple the introducer 104 to the therapy delivery element 106 so that the therapy assembly 100 exhibits a substantially 1:1 ratio of torque transmission from the fitting 122 to the fixation structures 118. In practice, the stiffness of the introducer 104 is sufficient to provide a substantially 1:1 ratio of torque transmission to the distal end 112 of the therapy delivery element 106. In particular, between about 90 percent to about 100 percent, or about 95 percent to about 100 percent, of torque 130 applied to fitting 122 is transmitted to the distal end 112.

As used herein, "torque transmission" refers to the efficiency with which a torque applied to a proximal end of a therapy assembly is delivered to a proximal end. Torque transmission for the present therapy assembly is preferably at least about 90% and more preferably at least about 95%. For example, if the proximal end is rotated about 10 degrees, the distal end will rotating at least about 9 degrees, and more preferably at least about 9.5 degrees. A therapy assembly according to the present disclosure preferably exhibits a torque transmission ratio in the range between about 1:1 to about 1:0.9, or about 1:1 to about 1:0.95.

To separate the fitting 122 and the introducer 104 from the therapy delivery element 106, the surgeon rotates the cap 128 to relieve the pressure on the o-ring 126 and slides the fitting 122 off. A variety of fittings 122 are suitable for this purpose, including the Luer lock assembly sold under part number PRJ4909 by Enpath Medical, Inc. located in Plymouth, Minn.

FIG. 8A illustrates one embodiment of interlock features 140 including one or more protrusions 142A, 142B, 142C, 142D ("142") located on outer surface 144 of the therapy delivery element 148. The protrusions 142 are configured to slide axially in corresponding grooves 146A, 146B, 146C, 146D ("146") formed along inner surface 150 of introducer 152. The protrusions 142 can be a variety of structures, such as bumps or ridges, and can be a variety of sizes. The protrusions 142 can be integrally molded or extruded on the therapy delivery element 148, overmolded onto the outer surface 144, or discrete structures bonded to the outer surface 144. Where discrete structures are used for the protrusions 142, the protrusions 142 can be made from a variety of bio-compatible polymeric or metal materials, such as for example, polyethylene terephthalate (PET), Nylon, polyether ether ketone (PEEK), polyproylene, high-performance polyethylenes, poly-L-lactide (PLLA), or polycaprolactone (PCL), urethane, silicone, Nitinol, stainless steel, MP35N, titanium, or any combination of these materials.

FIG. 8B illustrates alternate interlock features 160 including one or more protrusions 162A, 162B, 162C, 162D ("162") located on inner surface 164 of introducer 166. The protrusions 162 are configured to slide axially in corresponding grooves 168A, 168B, 168C, 168D ("168") formed along outer surface 170 of the therapy delivery element 172. The protrusions 162 are typically grooves molded or formed during extrusion of the introducer 166. The grooves 168 in the therapy delivery element 172 can be molded or formed, such as with laser ablation, thermal processes, and the like.

FIG. 8C illustrates alternate interlock features 180 including one or more discrete structures 182A, 182B, 182C, 182D ("182") engaged with opposing grooves 184, 186 at interface 188 of introducer 190 and therapy delivery element 192, respectively. In one embodiment, the discrete structures 182 are stylet wires used to stiffen the therapy assembly 192.

In another embodiment, the discrete structures 182 are wires used to steer the therapy assembly 180 during implantation. In particular, the wires 182 are secured near distal end of the introducer 190. Differential tensile and compressive forces are applied to the wires 182 to bias the distal end in a particular direction.

FIGS. 9A and 9B illustrate an alternate therapy assembly 200 in accordance with an embodiment of the present disclosure. Openings 202 in introducer 204 are aligned with electrodes 206 on therapy delivery element 208. After the therapy assembly 200 is positioned near the target nerve tissue, the surgeon activates the electrodes 206 to map the response, as discussed herein. The openings 202 permit the electrodes 206 to effectively stimulate the nerve tissue.

In one embodiment, the mapping process is completed by stimulating the nerve tissue through the openings 202 as illustrated in FIG. 9A. In another embodiment, the mapping process is completed by partially withdrawing the introducer 204 to fully expose the electrodes 206 as illustrated in FIG. 9B.

As illustrated in FIG. 9C, once the mapping process is completed and the surgeon is satisfied with placement of the therapy delivery element 208, the introducer 204 is withdrawn further to deploy fixation structures 210A, 210B, 210C, 210D ("210"). In the illustrate embodiment, the fixation structures 210 are shaped members that extend outward from central axis 212 the therapy delivery element 208. The fixation structures 210 can be a variety of shapes, such as hooks, wedge shape, curvilinear, and the like.

In the illustrated embodiment, the fixations structures 210 are generally symmetrical between the proximal ends 214 and the distal ends 216 relative to the central axis 212. As a result, the fixation structures 210 provide generally symmetrical resistance to displacement of the therapy delivery element 208 in either the proximal direction 228 or the distal direction 236.

The symmetrical resistance to displacement reduces the risk of the therapy delivery element 208 being inadvertently displaced in the distal direction 236, such as by patient movement, rather than in the proximal direction 228. For example, if the therapy delivery element 208 is subjected to cyclical push-pull forces, the angled tines shown in the prior art create a ratcheting-action that favors displacement in the distal direction 236 over the proximal direction 228. Over time, tined fixation structures can cause leads to migrate in the distal direction 236, resulting in misplacement of the electrodes 206 relative to the target nerve tissue. The present fixation structures 210 reduce the risk of ratcheting the therapy delivery element 208 in the distal direction 236.

The fixation structures 210 are attached to the therapy delivery element 208 at proximal ends 214 Distal ends 216 of the fixation structures 210, however, are not attached to the therapy delivery element 208 to facilitate deployment and subsequent collapse during removal of the therapy delivery element 208. In an alternate embodiment, the distal ends 216 are attached to a sliding member 215 (see FIG. 11B) configured to slide along the therapy delivery element 208.

The fixation structures 210 can be made from a variety of bio-compatible polymeric or metal materials, such as for example, polyethylene terephthalate (PET), Nylon, polyether ether ketone (PEEK), polyproylene, high-performance polyethylenes, bioabsorbale polymers, such as polyglutamic acid (PGA), poly-L-lactide (PLLA), or polycaprolactone (PCL), urethane, silicone, Nitinol, stainless steel, MP35N, titanium, or any combination of these materials. Any number of fixation structures 210 can be used, but typically there are about 2 to about 5. The fixation structures 210 are preferably elongated structures with a diameter in a range between about 0.004 inches and about 0.020 inches.

In one embodiment, the fixation structures are Nitinol wires heat-formed to retain a particular shape. When deployed from the introducer 204, the fixation structures resume the heat-formed shape. The heat formed Nitinol wires, however, will straighten or flatten if removal of the therapy delivery element 208 is necessary. The fixation structures 210 are preferably made from a Nitinol wire having a diameter in a range between about 0.004 to about 0.020 inches. When in the deployed configuration, the fixation structures 210 preferably extend outward from the therapy delivery element 208 an amount in a range between about 0.050 inches to about 0.150 inches.

Interlock features 218 includes a series of axial grooves 220 formed along inside surface of the introducer 204 (see e.g., FIG. 8A) that form a sliding interface with the fixation structures 210. The grooves 220 are formed offset from the openings 202 so that the fixation structures 210 do not inadvertently deploy into the openings 202. The interlock features 218 torsionally couple the introducer 204 to the therapy delivery element 208 along the entire length thereof. The grooves 220 also maintain the rotational orientation of the introducer 204 relative to the therapy delivery element 208 as the introducer 204 is withdrawn.

FIG. 9D illustrates the therapy delivery element 208 with the introducer 204 fully withdrawn. Tension force 224 can be applied to proximal end 226 to remove the therapy delivery element 208 from the patient. Proximal end 226 includes a fitting 122, such as illustrated in FIG. 7A, that locks the therapy delivery element 208 to the introducer 204. As the therapy delivery element 208 is displaced in proximal direction 228, the patient's tissue acts to apply compressive forces 232 on the fixation structures 210. The fixation structures 210 are compressed in direction 230 as distal ends 216 move in distal direction 236, facilitating removal of the therapy delivery element 208.

Figure 10A:
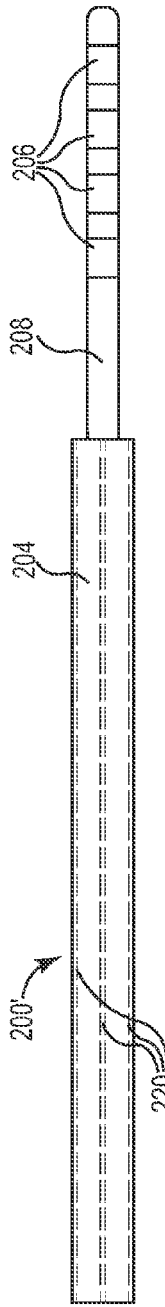
FIG. 10A illustrates an alternate embodiment of the therapy assembly of FIG. 9B.
Figure 10B:
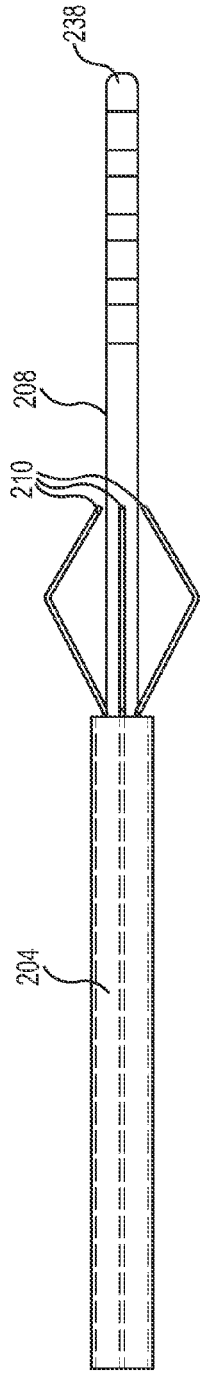
FIG. 10B illustrates an alternate embodiment of the therapy assembly of FIG. 9C.

FIGS. 10A and 10B illustrate an alternate therapy assembly 200' with the openings 202 in the introducer 204 removed in accordance with an embodiment of the present disclosure. The electrodes 206 are positioned outside of the introducer 204 to permit mapping. The grooves 220 are still provided on inside surface of the introducer 204 (see e.g., FIG. 8A) to form a sliding interface with the fixation structures 210 to torsionally couple the introducer 204 to the therapy delivery element 208. The grooves 220 also maintain the rotational orientation of the introducer 204 relative to the therapy delivery element 208 as the introducer 204 is withdrawn. When used with fitting 122, substantially all of the torque applied to the fitting 122 is transmitted to distal end 238 of the therapy delivery element 208.

Figure 11A:
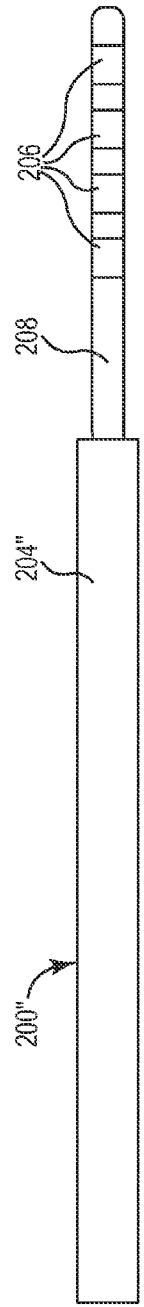
FIG. 11A illustrates another alternate embodiment of the therapy assembly of FIG. 9B.
Figure 11B:
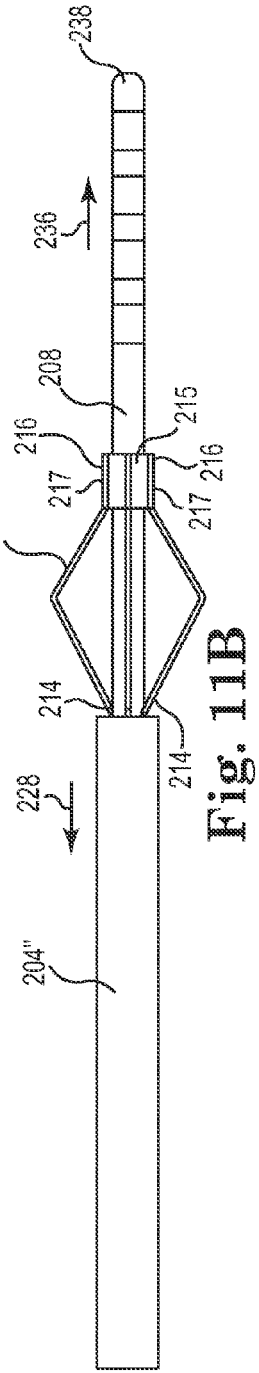
FIG. 11B illustrates another alternate embodiment of the therapy assembly of FIG. 9C.

FIGS. 11A and 11B illustrate an alternate therapy assembly 200" with the openings 202 and the grooves 220 removed from the introducer 204" in accordance with an embodiment of the present disclosure. Again, the electrodes 206 are positioned outside of the introducer 204" to permit mapping. The fixation structures 210 are configured to bias against the inside surface of the introducer 204 (see e.g., FIG. 8A) to torsionally couple the introducer 204" to the therapy delivery element 208.

In the illustrated embodiment, the distal ends 216 of the fixation structures 210 are attached to sliding member 215. The sliding member 215 can be a variety of structures, such as for example, an annular ring or sleeve. The distal ends 216 preferably include flared portions 217 that facilitate bonding to the sliding member 215. The flared portions 217 are preferably spot welded to the sliding member 215. In an alternate embodiment, the proximal ends 214 of the fixation structures are attached to the sliding member 215 and the distal ends 216 are attached to the therapy delivery element 208.

In operation, the sliding member 215 slides along the therapy delivery element 208 in both the proximal direction 228 and the distal direction 236. When the therapy delivery element 208 is inserted into the introducer 204", the sliding member 215 moves in the distal direction 236 as the fixation structures 210 are compressed to the collapsed configuration (see FIG. 11A). When the introducer 204" is retracted the sliding member 215 moves in the proximal direction 228 as the fixation structures 210 move to the deployed configuration (see FIG. 11B).

By attaching the distal ends 216 to the sliding member 215, the distal ends 216 do not get embedded in the surrounding tissue. The fixation structures 210 and sliding member 215 provide generally symmetrical resistance to displacement of the therapy delivery element 208 within the living body in either a proximal direction 228 or the distal direction 236.

The present sliding member 215 can be used with any of the embodiments disclosed herein. For example, when used with the introducer 204 of FIG. 10A, the flared portions 217 slide in the grooves 220. When used with fitting 122, substantially all of the torque applied to the fitting 122 is transmitted to distal end 238 of the therapy delivery element 208.

FIG. 12A through 12C illustrate an alternate therapy assembly 240 in accordance with an embodiment of the present disclosure. Openings 242 in introducer 244 are aligned with electrodes 246 on therapy delivery element 248. In one embodiment, the mapping process is completed by stimulating the nerve tissue through the openings 242 (see e.g., FIG. 9A). In another embodiment, the mapping process is completed by partially withdrawing the introducer 244 to fully expose the electrodes 246 (see e.g., FIG. 9B).

Once the mapping process is completed and the surgeon is satisfied with placement of the therapy delivery element 248, the introducer 244 is withdrawn to deploy hook-shaped fixation structures 250A, 250B, 250C, 250D ("250"). The fixation structures 250 are attached to the therapy delivery element 248 at proximal ends 252 by fastener 254. Distal ends 256 of the fixation structures 250 are not attached to the therapy delivery element 248 to facilitate deployment and subsequent fold inward during removal of the therapy delivery element 248 without the fastener 254. In another embodiment, the fixation structures 250 can be bonded to the therapy delivery element 248. As used herein "bonded" or "bonding" refers to adhesive bonding, solvent bonding, ultrasonic welding, thermal bonding, spot welding, mechanical interlock, compression fittings, and a variety of other techniques.

As best illustrated in FIG. 12B, the fastener 254 preferably includes protrusion 258 with surfaces 260 that resist displacement along central axis 268 of the therapy delivery element 248 in distal direction 262, while hooks 250 resist displacement in the opposite proximal direction 264.

The interlock features 270 include a series of axial grooves 272 formed along inside surface of the introducer (see e.g., FIG. 8A) that form an axial sliding interface with the fixation structures 250. The interlock features 270 torsionally couples the introducer 244 to the therapy delivery element 248 as discussed herein. The grooves 272 also maintain the rotational orientation of the introducer 244 relative to the therapy delivery element 248 as the introducer 244 is withdrawn. The grooves 272 are formed offset from the openings 242 so that the fixation structures 250 are not inadvertently deployed into the openings 242.

The embodiment of FIGS. 12A-12C can also be configured without the openings 242 in the introducer 244 and/or without the grooves 272, such as discussed in connection with FIGS. 10A-11B.

Although the fixations structures 250 are not symmetrical relative to the central axis 266, the wire forming the fixation structures 250 preferably has a diameter in a range of between about 0.004 inches to about 0.020 inches, which results in generally symmetrical resistance to displacement of the therapy delivery element 248 in either the proximal direction 264 or the distal direction 262. In particular, the fixation structures 250 are sufficiently flexible that ratcheting of the therapy delivery element 248 in the distal direction 262 does not occur.

Figure 13:
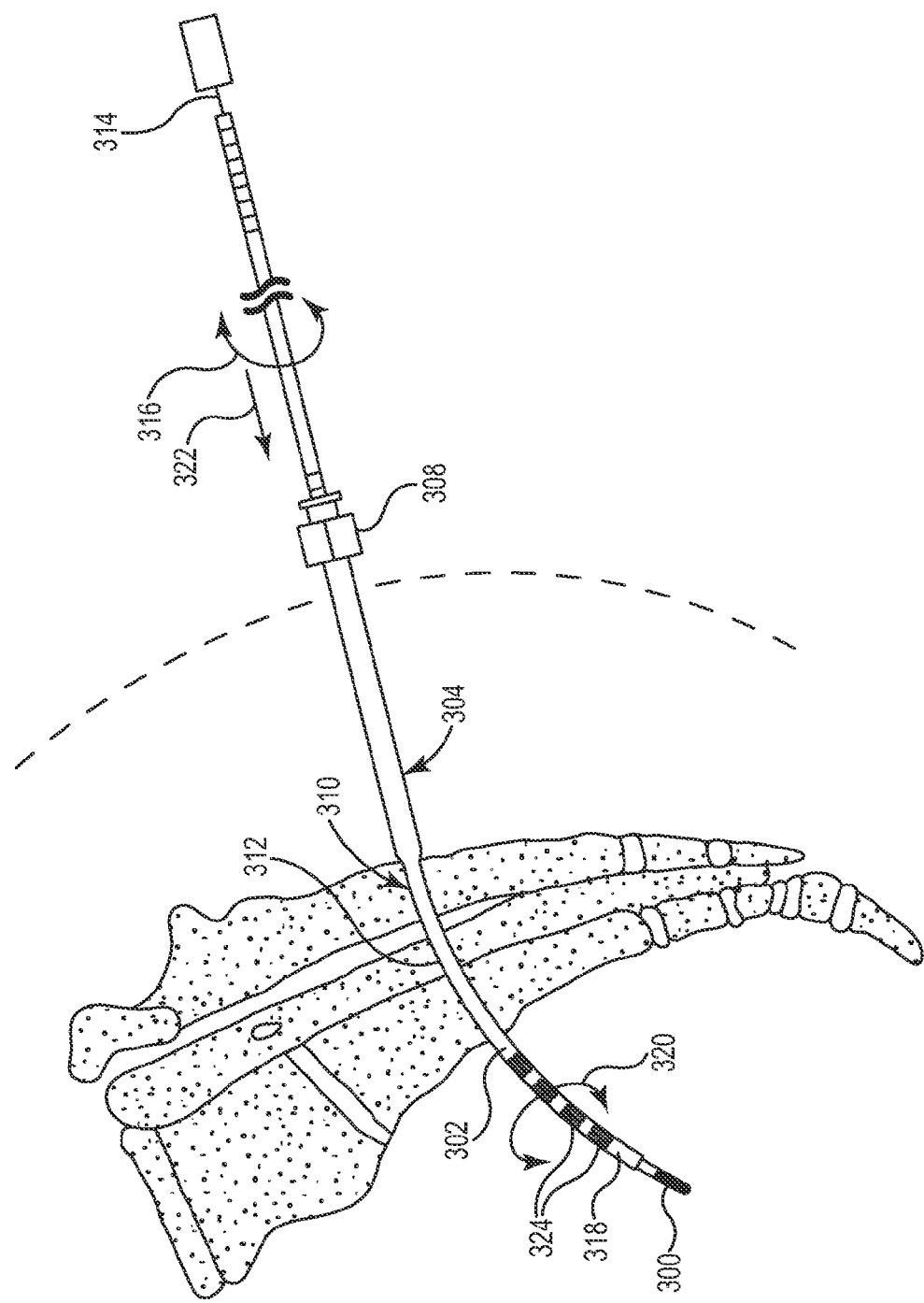
FIG. 13 illustrates a portion of a method of implanting a therapy delivery element in accordance with an embodiment of the present disclosure.

FIG. 13 illustrates one embodiment of implanting a therapy delivery element 300 located in introducer 302 in sacral nerve in accordance with an embodiment of the present disclosure. Interlock features 304 includes fixation structures 306 (see FIG. 12) and fitting 308 that secures the therapy delivery element 300 to the introducer 302 (see e.g., FIGS. 8A through 8C)

In one embodiment, therapy assembly 310 is advanced percutaneously at a selected angle through introducer 302 disposed at the selected foramen 312. The therapy delivery element 300 may be inserted near any of the sacral nerves including the S1, S2, S3, or S4, sacral nerves accessed via the corresponding foramen depending on the necessary or desired physiologic response. Stylet 314 is optionally located in the therapy delivery element 300 to increase stiffness and column strength of the therapy assembly 310.

The interlock features 304 transmit substantially all of torque 316 applied to luer lock 308 to distal end 318 of the therapy delivery element 300. In particular, the ratio between torque 316 and torque 320 is preferably in the range of between about 1:1 to about 1:0.9, or between about 1:1 to about 1:0.95.

In one embodiment, the introducer 302 is advance in direction 322 over a guide wire previously percutaneously advanced from the skin incision into the foramen to establish the angle of advancement. In yet another embodiment, a multi-part introducer can be employed having an inner introducer element that may be first advanced to the site by itself or over a previously introduced guide wire, and an outer introducer can be introduced over the inner element to dilate the tissue, whereupon the inner element is removed. Any percutaneous introduction tools and techniques may be employed that ultimately result in the therapy assembly 310 at the location of FIG. 11.

In one embodiment, nerve mapping is conducted through openings 324 in the introducer 302. In another embodiment, the introducer 302 is partially retracted to completely expose the electrodes 326 (see e.g., FIGS. 9B, 10A, and 11A).

Figure 14:
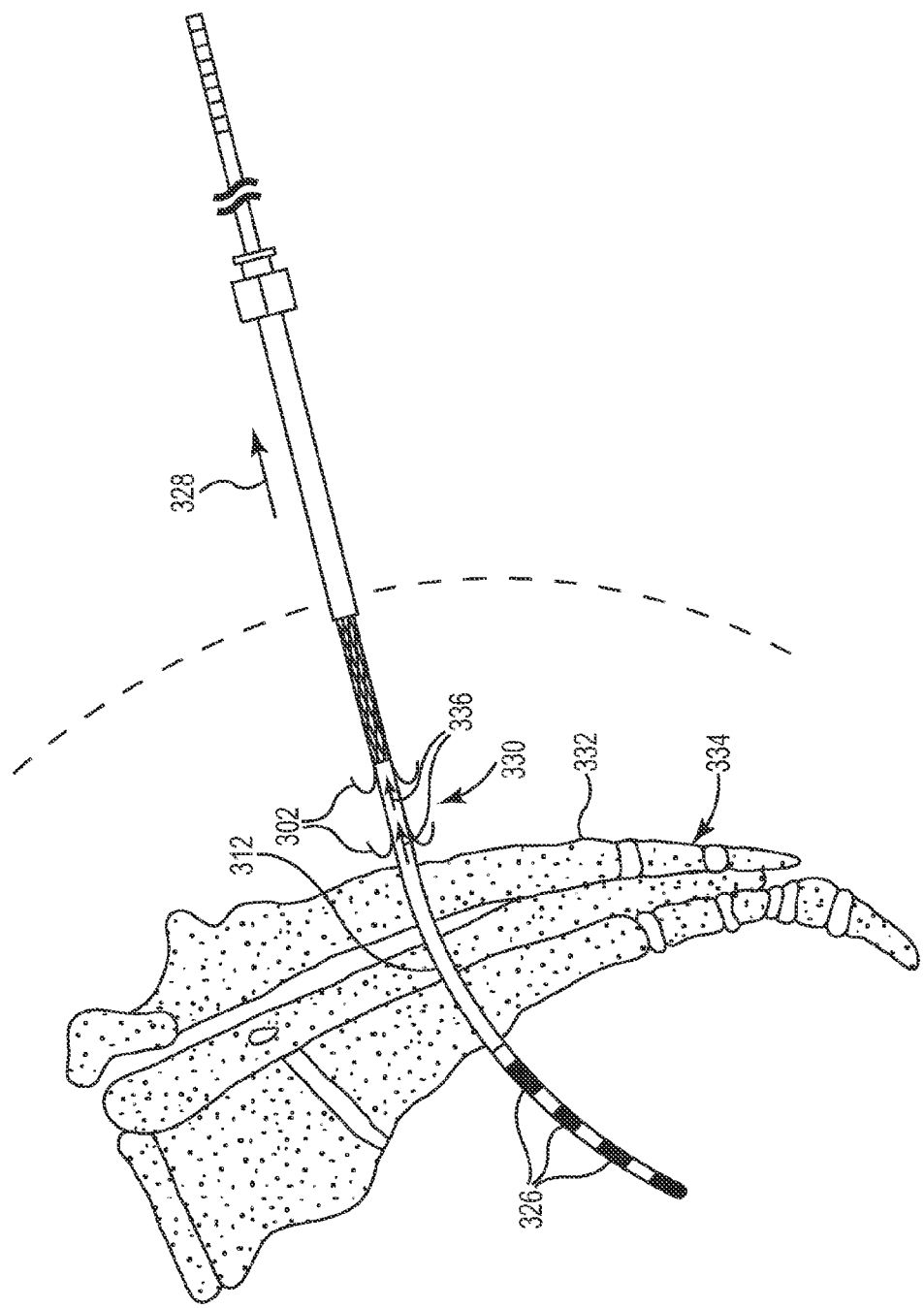
FIG. 14 illustrates a portion of a method of implanting a therapy delivery element in accordance with an embodiment of the present disclosure.

As illustrated in FIG. 14, the introducer 302 is retracted proximally in direction 328 after electrical testing of the therapy delivery element 300. The fixation structures 306 are released from the introducer 302 and engage with surrounding subcutaneous tissue 330 to secure the electrodes 326 relative to the foreman 312.

In the illustrated embodiment, two discrete fixation assemblies 336 each containing a plurality of fixation structures 306 are bonded to the therapy delivery element 300. The fixation structures 306 are preferably positioned to engage with the muscle tissue located along rear surface 332 of the sacrum 334. In one embodiment the fixation structures 306 can be seen under fluoroscopy to allow the physician to verify that the fixation structures 306 are deployed.

Figure 15:
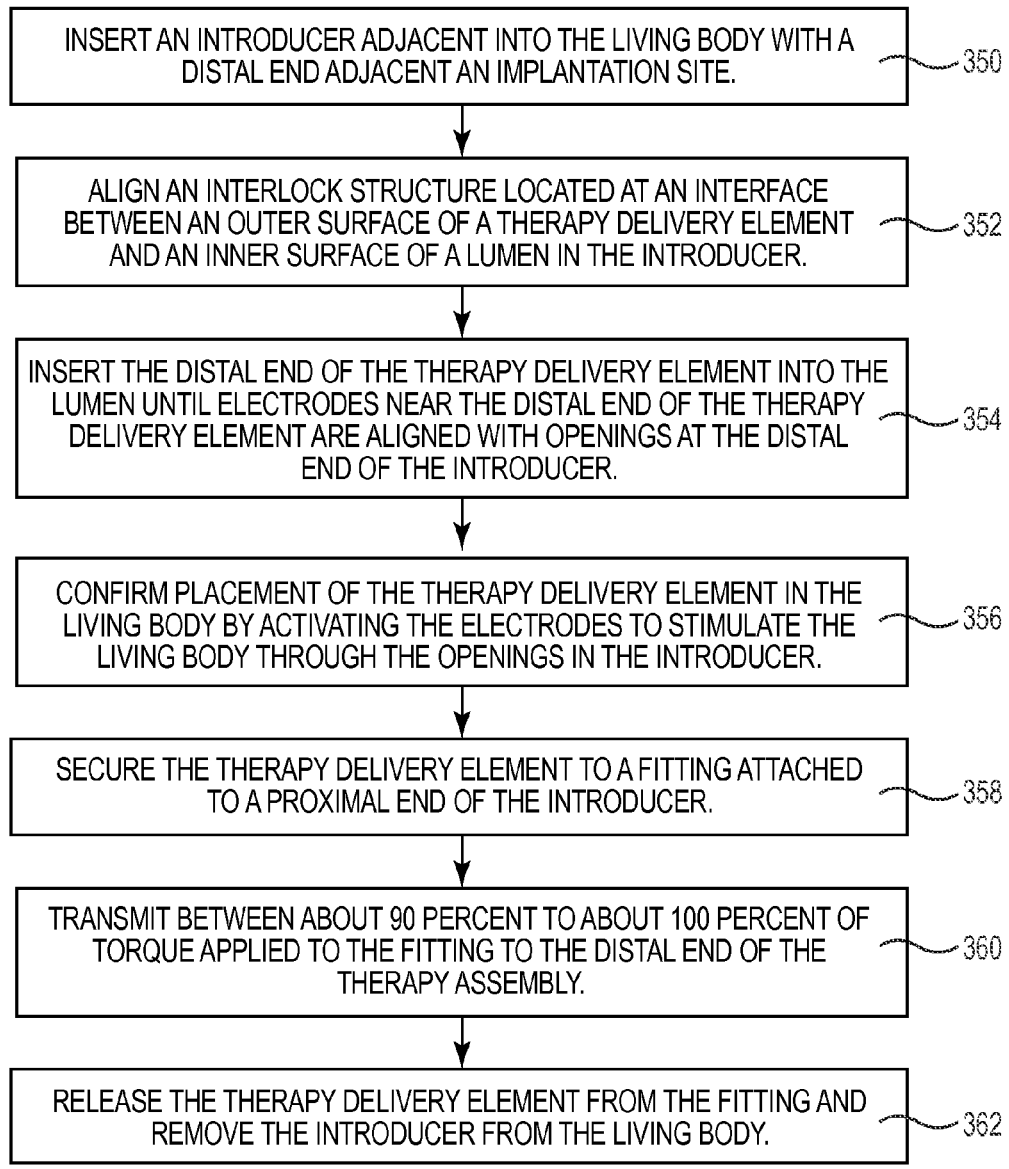
FIG. 15 is a flow chart of one method of using a therapy assembly in accordance with an embodiment of the present disclosure.

FIG. 15 is a flow chart directed to a method of implanting a therapy delivery element in a living body in accordance with an embodiment of the present disclosure. The method includes the steps of inserting an introducer adjacent into the living body with a distal end adjacent an implantation site (350). Interlock features are located at an interface between an outer surface of a therapy delivery element and an inner surface of a lumen in the introducer is aligned (352). The distal end of the therapy delivery element is inserted into the lumen until electrodes near the distal end of the therapy delivery element are aligned with openings at the distal end of the introducer (354). Placement of the therapy delivery element is confirmed in the living body by activating the electrodes to stimulate the living body through the openings in the introducer (356). The therapy delivery element is secured to a fitting attached to a proximal end of the introducer (358). Between about 90 percent to about 100 percent of torque applied to the fitting is transmitted to the distal end of the therapy assembly (360). The therapy delivery element is released from the fitting and the introducer is retracted from the living body (362).

Figure 16:
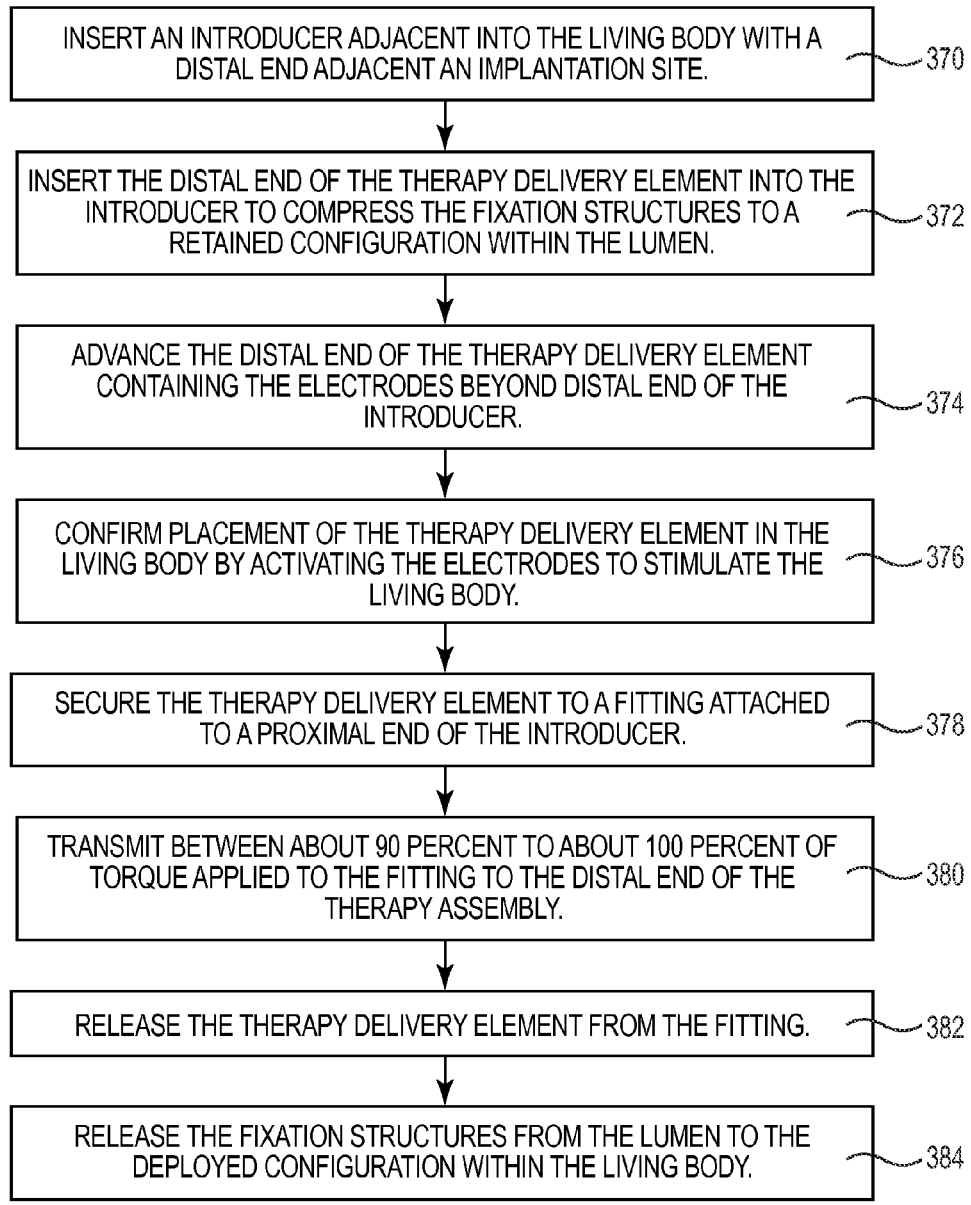
FIG. 16 is a flow chart of an alternate method of using a therapy assembly in accordance with an embodiment of the present disclosure.

FIG. 16 is a flow chart directed to an alternate method of implanting a therapy delivery element in a living body in accordance with an embodiment of the present disclosure. The method includes the steps of inserting an introducer adjacent into the living body with a distal end adjacent an implantation site (370). The distal end of the therapy delivery element is inserted into the introducer to compress the fixation structures to a collapsed configuration within the lumen (372). The distal end of the therapy delivery element containing the electrodes is advanced beyond the distal end of the introducer (374). Placement of the therapy delivery element is confirmed in the living body by activating the electrodes to stimulate the living body (376). The therapy delivery element is secured to a fitting attached to a proximal end of the introducer (378). Between about 90 percent to about 100 percent of torque applied to the fitting is transmitted to the distal end of the therapy assembly (380). The therapy delivery element is released from the fitting (382). The fixation structures are release from the lumen to a deployed configuration within the living body (384).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A therapy assembly configured for at least partial insertion in a living body, the therapy assembly comprising:
    a therapy delivery element comprising a proximal end with a plurality of electrical contacts configured to electrically couple with an implantable pulse generator and a distal end with a plurality of electrodes that are electrically coupled to the electrical contacts at the proximal end;
    an introducer with a lumen configured to receive the therapy delivery element;
    a plurality of fixation structures disposed radially around the therapy delivery element proximate the electrodes, the fixation structures comprising wires having a diameter in a range between about 0.004 inches and about 0.020 inches, the wires each having a first proximal end attached to the therapy delivery element and a second distal end that is not attached to the therapy delivery element and is configured to slide along the therapy delivery element, wherein the fixation structures are configured to collapse inwardly to a collapsed configuration when inserted into the lumen of the introducer and to deploy to a deployed configuration when the introducer is retracted, wherein, in the deployed configuration:
        each of the wires includes a portion intermediate the first proximal end and the second distal end, wherein the intermediate portion is spaced farther away from the therapy delivery element than the second distal end; and
        each of the fixation structures extends in a substantially distal direction from the first proximal end to the second distal end with the intermediate portion distal to the first proximal end and the second distal end distal to the intermediate portion; and
    a fitting located at a proximal end of the introducer that releasably locks the therapy delivery element to the introducer, wherein torque applied to the fitting is substantially transmitted to the distal end of the therapy assembly.

2. The therapy assembly of claim 1, wherein the fixation structures are configured to provide generally symmetrical resistance to displacement of the therapy delivery element within the living body in either a proximal direction or a distal direction along a central axis.

3. The therapy assembly of claim 1, wherein the fixation structures are generally symmetrical relative to a central axis of the therapy delivery element.

4. The therapy assembly of claim 1, comprising a plurality of openings in the introducer generally aligned with the electrodes.

5. The therapy assembly of claim 4, wherein the fixation structures are radially offset from the openings in the introducer.

6. The therapy assembly of claim 1, comprising a plurality of axially oriented grooves located on the inner surface of the introducer, the plurality of fixation structures, in the collapsed configuration, being retained in sliding engagement with the axial grooves to thereby substantially transmit torque applied to the proximal end of the introducer to the distal end of the therapy assembly.

7. The therapy assembly of claim 6, wherein the sliding engagement of the fixation structures in the axially oriented grooves maintains rotational alignment of openings in the introducer with the electrodes and prevents the fixation structures from deploying in the openings.

8. The therapy assembly of claim 1, wherein between about 90 percent to about 100 percent of torque applied to the fitting is transmitted to the distal end of the therapy assembly.

9. The therapy assembly of claim 1, comprising:
at least one pair of opposing axially oriented grooves located on the outer surface of the therapy delivery element and the inner surface of the introducer; and
at least one discrete structure slidingly engaging with both of the opposing axially oriented grooves.

10. The therapy assembly of claim 1, wherein the fixation structures are attached to a fastener that is bonded to the therapy delivery element.

11. The therapy assembly of claim 10, wherein the fastener comprises at least one surface oriented to resist displacement of the therapy delivery element in a distal direction.

12. The therapy assembly of claim 1, wherein each of the fixation structures is substantially symmetrical between the first end and the second end, each of the fixation structures being configured to provide substantially symmetrical resistance to displacement of the therapy delivery element in either a proximal direction or a distal direction.

13. A neurostimulation system comprising:
an implantable pulse generator;
a therapy delivery element comprising a proximal end with a plurality of electrical contacts configured to electrically couple with the implantable pulse generator and a distal end with a plurality of electrodes that are electrically coupled to the electrical contacts at the proximal end;
an introducer with a lumen configured to receive the therapy delivery element;
a plurality of fixation structures disposed radially around the therapy delivery element proximate the electrodes, the fixation structures comprising wires having a diameter in a range between about 0.004 inches and about 0.020 inches, the wires each having a first proximal end attached to the therapy delivery element and a second distal end that is not attached to the therapy delivery element and is configured to slide along and proximate the therapy delivery element, wherein the fixation structures are configured to collapse inwardly to a collapsed configuration when inserted into the lumen of the introducer and to deploy to a deployed configuration when the introducer is retracted, wherein, in the deployed configuration:
each of the wires includes a portion intermediate the first proximal end and the second distal end, wherein the intermediate portion is spaced farther away from the therapy delivery element than the second distal end; and
each of the fixation structures extends in a substantially distal direction from the first proximal end to the second distal end with the intermediate portion distal to the first proximal end and the second distal end distal to the intermediate portion; and
a fitting located at a proximal end of the introducer that releasably locks the therapy delivery element to the introducer, wherein torque applied to the fitting is substantially transmitted to the distal end of the therapy assembly.

14. The neurostimulation system of claim 13, wherein the fixation structures are generally symmetrical relative to a central axis of the therapy delivery element.

15. The neurostimulation system of claim 13, wherein the introducer includes a plurality of openings generally aligned with the electrodes with the therapy delivery element disposed within the lumen of the introducer, wherein the fixation structures are radially offset from the openings in the introducer.

16. The neurostimulation system of claim 13, wherein the introducer includes a plurality of axially oriented grooves located on the inner surface of the introducer, the plurality of fixation structures, in the collapsed configuration, being retained in sliding engagement with the axial grooves to thereby substantially transmit torque applied to the proximal end of the introducer to the distal end of the therapy assembly.

17. The neurostimulation system of claim 13, wherein each of the fixation structures is substantially symmetrical between the first end and the second end, each of the fixation structures being configured to provide substantially symmetrical resistance to displacement of the therapy delivery element in either a proximal direction or a distal direction.

18. A therapy assembly configured for at least partial insertion in a living body, the therapy assembly comprising:
a therapy delivery element including:
a proximal end including an electrical contact configured to electrically couple with an implantable pulse generator; and
a distal end including an electrode electrically coupled to the electrical contact at the proximal end;
an introducer with a lumen configured to receive the therapy delivery element; and
at least one fixation structure disposed on the therapy delivery element proximate the electrode, the fixation structure including a wire including a first proximal end attached to the therapy delivery element and a second distal end that is not attached to the therapy delivery element and is configured to slide along the therapy delivery element, wherein the fixation structure is configured to:
collapse inwardly to a collapsed configuration with insertion of the fixation structure into the lumen of the introducer; and
deploy to a deployed configuration with removal of the introducer from around the fixation structure, wherein, in the deployed configuration:
the wire of the at least one fixation structure includes a portion intermediate the first proximal end and the second distal end, wherein the intermediate portion is spaced farther away from the therapy delivery element than the second distal end; and the wire of the at least one fixation structure extends in a substantially distal direction from the first proximal end to the second distal end with the intermediate portion distal to the first proximal end and the second distal end distal to the intermediate portion.

19. The therapy assembly of claim 18, comprising a fitting located at a proximal end of the introducer, the fitting configured to releasably lock the therapy delivery element to the introducer, wherein torque applied to the fitting is substantially transmitted to the distal end of the therapy assembly.

20. The therapy assembly of claim 18, wherein the at least one fixation structure includes a plurality of fixation structures disposed radially around the therapy delivery element proximate the electrodes.

21. The therapy assembly of claim 20, wherein the fixation structures are generally symmetrical relative to a central axis of the therapy delivery element.

22. The therapy assembly of claim 18, wherein the introducer includes at least one axially oriented groove located on the inner surface of the introducer, the at least one fixation structure, in the collapsed configuration, being retained in sliding engagement with the axial groove to thereby substantially transmit torque applied to a proximal end of the introducer to the distal end of the therapy delivery element.

23. The therapy assembly of claim 18, wherein the at least one fixation structure is substantially symmetrical between the first end and the second end, the at least one fixation structure being configured to provide substantially symmetrical resistance to displacement of the therapy delivery element in either a proximal direction or a distal direction.

* * * * *

UNITED STATES PATENT AND TRADEMARK OFFICE
CERTIFICATE OF CORRECTION

PATENT NO.         : 9,095,700 B2                                    Page 1 of 1
APPLICATION NO.    : 13/571987
DATED              : August 4, 2015
INVENTOR(S)        : Lawrence Kane et al.

It is certified that error appears in the above-identified patent and that said Letters Patent is hereby corrected as shown below:

On The Title Page, item (73) Assignee delete "Greatbach" and insert --Greatbatch--

Signed and Sealed this
Fifth Day of January, 2016

Michelle K. Lee
*Director of the United States Patent and Trademark Office*